US012084471B2

United States Patent
Surace et al.

(10) Patent No.: US 12,084,471 B2
(45) Date of Patent: *Sep. 10, 2024

(54) AMINO ACID DERIVATIVE OF GLUCOSAMINE STIMULATING EXTRACELLULAR MATRIX SYNTHESIS AND PHARMACEUTICAL COMPOSITION COMPRISING THE SAME

(71) Applicant: CARTILAGO S.R.L., Maglie (IT)

(72) Inventors: Filippo Surace, Otranto (IT); Roberto Scandurra, Rome (IT)

(73) Assignee: CARTILAGO S.R.L., Maglie (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/321,363

(22) Filed: May 22, 2023

(65) Prior Publication Data

US 2023/0399353 A1    Dec. 14, 2023

Related U.S. Application Data

(63) Continuation of application No. 17/277,876, filed as application No. PCT/IB2019/057896 on Sep. 19, 2019, now Pat. No. 11,685,760.

(30) Foreign Application Priority Data

Sep. 20, 2018    (IT) .......................... 102018000008758

(51) Int. Cl.
| A61K 9/00 | (2006.01) |
| A61K 9/06 | (2006.01) |
| A61K 31/7008 | (2006.01) |
| C07H 15/207 | (2006.01) |

(52) U.S. Cl.
CPC ............. *C07H 15/207* (2013.01); *A61K 9/00* (2013.01); *A61K 9/0019* (2013.01); *A61K 9/06* (2013.01); *A61K 31/7008* (2013.01)

(58) Field of Classification Search
None
See application file for complete search history.

(56) References Cited

U.S. PATENT DOCUMENTS 11,685,760 B2 *    6/2023    Surace ..................... A61K 9/06
                                                           514/42

FOREIGN PATENT DOCUMENTS

IT    RM20090369 A1    1/2011

OTHER PUBLICATIONS

Battistelli et al., "Cell and matrix morpho-functional analysis in chondrocyte micromasses," Microscopy Research and Technique, 67:286-295 (2005).
D'Abusco et al., "Effects of intra-articular administration of glucosamine and a peptidyl-glucosamine derivative in a rabbit model of experimental osteoarthritis: a pilot study", Rheumatology International, Springer, Berlin, DE, vol. 28, No. 5, Oct. 9, 2007, pp. 437-443, XP019587694.
Doherty et al., "Amino acid derivatives of D-glucosamine," Journal of the American Chemical Society, vol. 75, No. 14, Jul. 1, 1953, pp. 3466-3468, XP009129110.
d'Abrusco et al., "A peptidyl-glucosamine derivative affects IKKa kinase activity in human chondrocytes," Arthritis Research & Therapy 2010, 12:R18.
d'Abrusco et al., "Glucosamine affects intracellar signalling through inhibition of mitrogen-activated protein kinase phosphorylation in human chondrocytes," Arthritis Research & Therapy, vol. 9, No. 5, 2007.
Giordano et al., "Synthesis and properties of D-glucosamine N-peptidyl derivatives as substrate analog inhibitors of papain and cathepsin B", European Journal of Medicinal Chemistry, Elsevier, Paris, FR, vol. 26, No. 8, Nov. 1, 1991, pp. 753-762, XP023870484.
Goldring, M., "Update on the biology of the chondrocyte and new approaches to treating cartilage diseases," Best Practice and Research Clinical Rhuematology, vol. 20, No. 5, pp. 1003-1025, 2006.
International Search Report and Written Opinion of the ISA for PCT/IB2019/057896 dated Jan. 29, 2020, 13 pages.
Stoppoloni et al., "Effect of glucosamine and it's peptidyl-derivative on the production of extracellular matrix components by human primary chondrocytes," Osteoarthritis and Cartilage 23 (2015) 103-113.
Veronesi et al., "Chondroprotective activity of N-acetyl phenylalanine glucosamine derivative on knee joint structure and inflammation in a murine model of osteoarthritis," Osteoarthritis and Cartilage, Nov. 1, 2016, 11 pages, XP055347292.

* cited by examiner

*Primary Examiner* — Traviss C Mcintosh, III
(74) *Attorney, Agent, or Firm* — NIXON & VANDERHYE

(57) ABSTRACT

The present patent application relates to the use of an innovative amino acid derivative of glucosamine having the Formula 1 of the general structure which follows, or of a pharmaceutical composition which contains it as a single active ingredient or in association with one or more further active ingredients for the preparation of a medicament for the treatment or prophylaxis of diseases involved mainly with the regulation of the turnover of macromolecules that make up the ECM of connective tissue in general and more specifically of the cartilage.

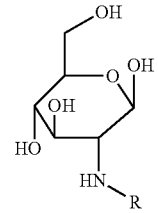

(Formula 1)

19 Claims, No Drawings

AMINO ACID DERIVATIVE OF GLUCOSAMINE STIMULATING EXTRACELLULAR MATRIX SYNTHESIS AND PHARMACEUTICAL COMPOSITION COMPRISING THE SAME

CROSS REFERENCE TO RELATED APPLICATIONS

This application is a Continuation of application Ser. No. 17/277,876, filed on Mar. 19, 2021, which is the U.S. national phase of International Application No. PCT/IB2019/057896, filed Sep. 19, 2019, which designated the U.S. and claims priority to IT Patent Application No. 102018000008758 filed Sep. 20, 2018, the entire contents of each of which are hereby incorporated by reference.

BACKGROUND OF THE INVENTION

Field of the Invention

As is known, the human body and its component organs are supported and held together by tissues traditionally referred to as connective, a term that indicates their structural and supporting role. However the function of the connective tissues goes far beyond that of support, acting as a link for the other tissues, participating in the defense mechanisms of the organism and ensuring the nourishment to tissues that are not vascularized.

All the different types of connective tissues consist of two essential components: a cell population and an extracellular matrix (ECM), the latter consisting of an amorphous component and a fibrous component and in which the relative proportions of each of these two components vary depending on the type of connective tissue considered.

The extracellular matrix (ECM) is an organized network of extracellular materials present in the vicinity of the plasma membrane, which can play a key role in determining the shape and activities of a cell. Its components are subjected to a continuous remodeling necessary for the proper functioning of different physiological processes, with a rhythm that slows down with age. Therefore an inadequate remodeling is at the base of the onset of different diseases that among other things concern both the locomotor apparatus and the skin (Naba et al, 2015).

A particular type of specialized connective tissue is the cartilage tissue. The cartilage is in fact defined as a supporting connective tissue, consisting of a single cell type, the chondrocytes and an abundant extracellular matrix (ECM). The chondrocytes constitute 2-5% of said tissue and are responsible for the production of the components of the extracellular matrix and for the continuous remodeling of the latter. The matrix consists of collagen fibers and macromolecular aggregates, as well as proteoglycans, among which the most represented is aggrecan. The cartilage tissue is subjected to continuous remodeling, a process that involves maintaining a delicate balance between the anabolic and catabolic pathways.

The main pathology affecting cartilage tissue is osteoarthritis (OA), which is the most common type of joint disease forming part of musculoskeletal disorders and which is characterized by pain, erythema, swelling, peri- and intra-articular effusion, motor impairment and functional impairment at the joint level. This pathology, in fact, is characterized by a structural alteration of the fundamental substance of the articular cartilage, determining its wear and defibration and reducing its ability to absorb mechanical stresses during loading and movement; following this, the underlying bone, although reacting with an increase in osteogenesis, ends up undergoing deformations. In the slowly evolving form, OA can be considered a paraphysiological condition of wear of the joint, an expression of aging, while in the fast-changing form it represents a real disease. OA presents mainly degenerative aspects, but also more or less intense signs of phlogosis. During the progression of OA, an imbalance is determined between anabolic and catabolic processes, responsible for remodeling the cartilaginous matrix. The secretion of pro-inflammatory cytokines causes a decrease in the synthesis of new matrix, while the erosion of cartilage is consequent to the hyper-activation of metalloproteases. The final outcome of the osteoarthritic process is the total blockage of the affected joint with loss of its functionality.

Description of the Related Art

Different types of approaches are already known in OA therapy, ranging from preventive measures to pharmacological, physical and surgical treatments.

Except for the surgical therapy of OA concerning prosthetic replacement procedures, which generally lead to the complete disappearance of pain symptoms and improvement of joint function, but with all the limitations represented by the execution of a surgical procedure and a non-unlimited duration of implanted prostheses, the goal of all therapeutic approaches aimed at OA is unfortunately only to improve the patient's quality of life through pain control, preservation of joint function and slowing of joint degradation.

Entering the field of application of the present invention it is necessary to focus attention on the pharmacological therapy of OA, whose drugs can be divided into symptomatic, which aim to fight pain, and drugs which act on the structure of articular cartilage called chondroprotectors. Non-steroidal anti-inflammatory drugs (NSAIDs) represent the first choice therapy for the treatment of pain and of the inflammatory phases of the disease. A more effective or more indicated NSAID for the symptomatic treatment of OA has not been recognized. The choice of the type of NSAID depends on tolerability, on certain characteristics linked to the molecule such as duration and selectivity of action, and on the clinical response.

Among the most used ones we may mention: ibuprofen, nimesulide, naproxen, ketoprofen, diclofenac. The limit of use of these drugs is related to their side effects, in particular the harmfulness to the stomach, which does not allow a continuous use thereof. Paracetamol is widely used for its analgesic action, especially in patients at gastro-intestinal risk or with other contraindications to the use of NSAIDs. Since some years in our country opioid analgesics can be used for OA, useful in subjects who do not tolerate NSAIDs or who do not respond very well to non-opiate analgesics. Among the most used are codeine and tramadol, which can also be taken in association or in combination. Other therapies used, which can be used occasionally and in a specialized environment, are intra-articular infiltrations with a cortisone preparation or based on hyaluronic acid, which however have only a limited effect over time.

On another level, chondroprotective drugs represent one of the new therapeutic perspectives in the treatment of OA, as they directly influence the cartilage metabolism, inhibiting degenerative processes and/or stimulating the synthesis of new ECM by chondrocytes. From the studies carried out on these new substances, the one that has shown greater efficacy is glucosamine of natural origin, which should be able to inhibit the production of cartilage inflammatory factors, block its degradation and promote the production of new cartilage.

Although the other candidate substances for this role are still under study, including hyaluronic acid itself, chondroitin sulfate, diacerin and soya and avocado extracts, their mechanism of action has not been completely clarified, therefore their effectiveness is not accepted by all (Cutolo et al, 2015).

With regard to future therapeutic perspectives, major hopes derive from advances in tissue engineering: "the implantation of autologous chondrocytes", that is, the grafting of cartilaginous cells taken from the same patient, is obtaining good results. However, it is still a limited intervention, which appears to be determining only in young patients, on some joints and in cases of modest lesions that have not affected the underlying bone (B. L. Kidd et al, 2007).

As far as epidemiology is concerned, osteoarthritis affects all vertebrates and in humans the frequency of the disease is very high, a disease that afflicts a large part of the world population (Loeser et al, 2012), particularly the average and senile age population. Radiological signs of OA can be found in over 80% of people between the ages of 50 and 65, although the symptomatology in the same age group is present in about 20% of women and in 15% of men. In Italy the pathology affects about 4 million people and represents one of the most frequent reasons for resorting to a medical examination in general medical practices.

As described above and in relation to the rise of the average life age, OA has become a social problem of primary importance, with negative repercussions not only on the quality of life of patients but also involving considerable socio-economic burdens which inevitably weigh on national health systems.

SUMMARY OF THE INVENTION

Consequently, the general aim of the present invention is to realize a new pharmacological pathway, able to stop the evolutionary process of this pathology and therefore to prevent the possible debilitating damage that may derive from it and at the same time, able to make the cartilage reacquire a structure very similar to the healthy one and therefore, as far as possible, deprived of the pathological aspects described above.

Other advantages of the invention will become apparent from the detailed description of an embodiment thereof provided by way of non-limiting example, illustrated below.

The compounds disclosed in the present patent application have been discovered to exert surprising and unexpected biological effects. In particular, the compounds referred to or the pharmaceutical compositions comprising them have shown an ability to appropriately stimulate the components of the (ECM) in the connective tissue and specifically in the cartilaginous tissue, causing it to reacquire a structure completely similar to the pre-existing healthy structure, or in the case of cartilage without the degenerative signs for example of osteoarthrosic nature.

Said inventive compounds generally consist of amino acid derivatives of glucosamine and more preferably represented by an N-acetyl-phenylalanine derivative of glucosamine, on whose compound the majority of the experimental tests which follow are concentrated.

What just stated derives in general from an in-depth study of the inventors performed with in vitro and in vivo methods, able to validate the mechanism of action and the biological activity of the innovative amino acid derivatives of glucosamine.

The above class of compounds and more specifically the N-acetyl-phenylalanine derivative of glucosamine, has been studied in in vivo models of OA both in rabbit and in mice, finding that the intra-articular administration of said compound in the osteoarthritic knees of rabbits or mice stimulated the synthesis of new ECM, making the cartilage regain a structure very similar to the healthy one, free of osteoarthritis and thus suggesting that this class of compounds has an important regenerative effect.

To clarify the molecular mechanism, glucosamine-derived N-acetyl-phenylalanine has been studied in vitro, using primary cultured chondrocytes. The chondrocytes were stimulated with IL-1 in order to study the inflammatory pathway, controlled by the Activator Protein (AP)-1. Specifically, said N-acetyl-phenylalanine glucosamine derivative was unexpectedly effective in first inhibiting the phosphorylation of two kinases, JNK and p38, and consequently influencing the activation of c-jun, one of the components of AP-1. The efficacy of interfering with the inflammatory pathway controlled by the transcription factor Nuclear Factor-κB (NF-κB) was then analyzed, which in turn is controlled by the IKK complex consisting of two IKKα and IKKβ kinases. Said N-acetyl-phenylalanine derivative of glucosamine inhibited the translocation in the nucleus of the IKKα kinase, which exerts its activity above all in that cellular district, selectively inhibiting the kinase activity of IKKα but not IKKβ.

Finally, in order to understand which intracellular pathways are activated by said N-acetyl-phenylalanine derived from glucosamine to stimulate ECM synthesis, further in vitro studies in human primary chondrocytes were conducted. In order to simulate physiological conditions, the culture of human chondrocytes was carried out in three dimensions, cultivating the cells in the form of spheroids. The results unexpectedly showed that the aforementioned inventive compound stimulated the synthesis of type II collagen, characteristic of cartilage tissue. In addition, through these experiments it was found that if the cells are treated simultaneously with glucosamine and said N-acetyl-phenylalanine derived from glucosamine, a synergistic effect is obtained, with an even greater production of type II collagen, inducing the expression of a growth factor, IGF-1 (Insulin Growth Factor), and a transcription factor SOX-9 (Sry-related HMG bOX-containing genes), which control the synthesis of ECM, thus determining this interesting anabolic effect exercised by the association of the two molecules.

Another important and unexpected discovery is that the aforementioned amino acid derivatives of glucosamine and more specifically the N-acetyl-phenylalanine derivative of glucosamine is able to stimulate the expression of the enzyme synthetase of hyaluronic acid (HAS-2) and consequently the production of hyaluronic acid (HA).

Another promising discovery for the purposes of carrying out the present invention is that the aforementioned class of inventive compounds has proved to be particularly effective also on primary human fibroblasts, which when grown in three dimensions, like spheroids, have produced a rather high amount of type I collagen with respect to spheroids grown in the absence of said innovative compound. Furthermore, the N-acetyl-phenylalanine derivative of glucosamine has also been added to the culture medium of fibroblasts stimulated with UVB, to such an extent as to simulate the irradiation of solar UVB, finding that the molecule was able to counteract the inflammatory pathways stimulated by UVB and also to restore the synthesis of type I collagen, which is instead blocked by UVB treatment. This discovery promptly aroused in the inventors an interest in the ability of this class of products to intervene in the remodeling of the cutaneous ECM, in which the relative alteration of turnover leads to atrophy of the skin, with consequent aging of the skin and in some cases even to onset of skin cancer processes.

Therefore, starting from the promising results described both in the aforementioned in vivo and in vitro studies, the inventors of the following invention have developed the use of the aforementioned innovative amino acid derivative of glucosamine, which generally consists in the treatment or prophylaxis of the pathologies involved mainly with the regulation of the turnover of the macromolecules that make up the ECM of the connective tissue and specifically of the cartilaginous tissue, which for illustrative and non-limiting purposes will be described in the detailed description that follows.

Other features of the present invention are described in the following detailed description of one or more specific embodiments thereof.

DETAILED DESCRIPTION OF THE INVENTION

It should be noted that hereinafter, only some of the possible embodiments of the present invention will be illustrated, by way of non-limiting example, it being possible to describe many others thereof on the basis of the particular technical solutions identified.

The present patent application relates to the use of an innovative amino acid derivative of glucosamine, or of a pharmaceutical composition which contains it as a single active ingredient or in association with one or more further active ingredients for the preparation of a medicament for the treatment or prophylaxis of diseases involved mainly with the regulation of the turnover of macromolecules that make up the ECM of connective tissue and more specifically of the cartilage tissue.

Accordingly, the general aim of the present invention is to provide a new pharmacological method capable of stopping the evolutionary pathway of osteoarthritis and thus of preventing the possible debilitating damage that may derive therefrom.

A further object according to the present invention is to provide a drug capable of stimulating the endogenous synthesis of a new extracellular matrix.

An even more particular object is to make the cartilage reacquire a structure very similar to the healthy one, that is, deprived of degeneration due to the osteoarthritic process or in any case of degeneration due to other causes including that due to hyper-stress from an intense sporting activity, appropriately stimulating the cells to produce the components of the matrix, as well as the collagens, the proteoglycans, the glycosaminoglycans and the aggrecan.

A further object relates to the aforementioned ability of this class of products to restore the synthesis of type I and type II collagen due to the activity of fibroblasts, intervening in the remodeling of the cutaneous ECM and therefore to be used appropriately in the treatment of skin aging by counteracting skin atrophy, and in some cases preventing and suggesting new therapeutic strategies for the treatment of skin cancers.

Said inventive compounds generally consist of amino acid derivatives of glucosamine having the following Formula 1 of general structure:

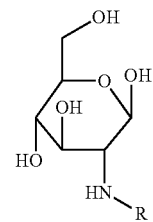

Formula 1 wherein the group R represents an amino acid, an N-acyl derivative of an amino acid or an N-acyl derivative of a peptide and wherein the amine group of glucosamine is bound by carbamide bond to the carboxyl side chain of said amino acid.

A particularly preferred embodiment of the present invention provides that said inventive compounds are preferably represented by an N-acetyl-phenylalanine derived from glucosamine having the following Formula 2 of structure:

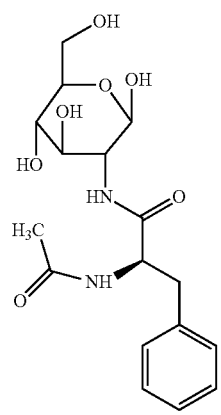

Formula 2

The compound having the Formula 1 according to the present invention or the one having the Formula 2 can exist as a pharmaceutical composition which contains it alone or in association with one or more active ingredients, together with one or more excipients or carriers suitable for the route of administration chosen and prepared according to the well-known standards of good manufacturing technology and pharmaceutical legislation.

In the light of the above experimental evidence, a preferred embodiment of the present invention contemplates to provide a pharmaceutical composition suitable for the parenteral administration route and more specifically for the intra-articular or trans-dermal route, by implementing an injection solution for intra-articular or intra-dermal use consisting of a compound having Formula 1 or of a pharmaceutically acceptable salt, solvate, hydrate or stereoisomer thereof at a concentration comprised between 0.5% by weight and 4.5% by weight and more preferably between 1% by weight and 3% by weight, together with suitable and known carriers for said administration route.

A further preferred embodiment provides that the aforementioned pharmaceutical composition consists of an association of active ingredients consisting of the inventive amino acid derivative of glucosamine having Formula 1 or of a pharmaceutically acceptable salt, solvate, hydrate or stereoisomer thereof at a concentration of between 0.5% by weight and 4.5% by weight and more preferably between 1% by weight and 3% by weight and even more preferably by 2.5% by weight and by glucosamine and/or hyaluronic acid, each at a concentration ranging from 0.1% by weight to 0.4% by weight and more preferably equal to 0.25%. In particular, the aforementioned pharmacological association arose from experimental evidence that demonstrated that the addition of glucosamine has a synergistic effect on the pharmacological activity of the drug, and that the addition of hyaluronic acid is suggested precisely by the properties of this molecule capable of providing greater viscosity to the preparation, with consequent lubricating effect when administered in the joints. In particular, it should be noted that although all human skeletal joints can be subject to and therefore benefit from the aforementioned administration, preferably the knee is the preferred one.

A further embodiment according to the present invention for the purpose of the therapeutic and prophylactic effect referred to above, has the object of providing a pharmaceutical composition suitable for the topical administration route by making a cream consisting of a compound having Formula 1 or of a pharmaceutically acceptable salt, solvate, hydrate or stereoisomer thereof at a concentration comprised between 0.1% by weight and 2% by weight and more preferably equal by 1% by weight in the base cream.

The present invention has been described for illustrative but non-limiting purposes, according to some preferred embodiments thereof, but it is to be understood that any variations and/or modifications may be made by the man skilled in the art without thereby departing from the relative scope of protection as defined by the following dependent claims.

The invention claimed is:

1. An injectable solution pharmaceutical composition comprising an amino acid derivative of glucosamine having the following Formula 1 of general structure:

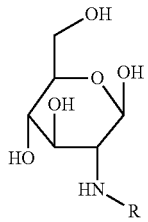

(Formula 1)

or the pharmaceutically acceptable salt, solvate, hydrate or stereoisomer thereof, wherein the group R represents an amino acid, an N-acyl derivative of an amino acid or an N-acyl derivative of a peptide and wherein the amine group of glucosamine is bound by amide bond to the carboxyl side chain of said amino acid; wherein the pharmaceutical composition comprises the amino acid derivative of glucosamine at a concentration of between 0.5% by weight and 4.5% by weight, together with carriers suitable for injection.

2. The injectable solution pharmaceutical composition according to claim 1, wherein the amino acid derivative of glucosamine consists of an N-acetyl-phenylalanine derivative of glucosamine having the following structural Formula 2:

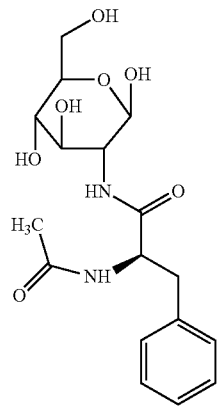

(Formula 2)

or the pharmaceutically acceptable salt, solvate, hydrate or stereoisomer thereof.

3. The injectable solution pharmaceutical composition according to claim 1, wherein the composition is suitable for the intra-articular route.

4. The injectable solution pharmaceutical composition according to claim 1, wherein the composition is suitable for the intra-dermal route.

5. The injectable solution pharmaceutical composition according to claim 1, comprising the amino acid derivative of glucosamine at a concentration of between 1% by weight and 3% by weight, together with carriers suitable for injection.

6. The injectable solution pharmaceutical composition according to claim 1, further comprising glucosamine.

7. The injectable solution pharmaceutical composition according to claim 6, wherein glucosamine has a concentration ranging from 0.1% by weight to 0.4% by weight.

8. The injectable solution pharmaceutical composition according to claim 1, further comprising hyaluronic acid.

9. The injectable solution pharmaceutical composition according to claim 8, wherein hyaluronic acid has a concentration ranging from 0.1% by weight to 0.4% by weight.

10. A method for therapeutic regeneration of connective tissue, comprising administering via injection an effective amount of the injectable solution pharmaceutical composition of claim 1 to a patient in need thereof.

11. A method according to claim 10, wherein the method is a method for therapeutic regeneration of connective tissue following degenerative processes of the articular cartilage of an osteoarthritic nature, in a human being, following degenerative processes due to a hyper-stressing of the articular cartilage.

12. A method according to claim 11, wherein the method is a method for the treatment of osteoarthritis.

13. The method according to claim 10, wherein the injection comprises injection via the intra-articular route i.e. intra-articular injection.

14. The method according to claim 13, wherein the injection via the intra-articular route i.e. intra-articular injection comprises injection into the knee of a patient.

15. The method according to claim 10, wherein the injection comprises injection via the intra dermal route i.e. intra-dermal injection.

16. The method according to claim 10, wherein the patient in need thereof is a mammal.

17. The method according to claim 16, wherein the patient in need thereof is a human.

18. A method for the protection against inflammatory damage to connective tissue, comprising administering via injection an effective amount of the injectable solution pharmaceutical composition of claim 1 to a patient in need thereof.

19. A method for the treatment of inflammatory damage to connective tissue, comprising administering via injection an effective amount of the injectable solution pharmaceutical composition of claim 1 to a patient in need thereof.

* * * * *